United States Patent [19]

Paust et al.

[11] Patent Number: 5,338,888
[45] Date of Patent: Aug. 16, 1994

[54] PREPARATION OF E,Z-BUTENEDIAL BIS(DIALKYL ACETALS)

[75] Inventors: Joachim Paust, Neuhofen; Wolfgang Krause, Mannheim, both of Fed. Rep. of Germany

[73] Assignee: BASF Aktiengesellschaft, Ludwigshafen, Fed. Rep. of Germany

[21] Appl. No.: 86,028

[22] Filed: Jul. 6, 1993

[30] Foreign Application Priority Data

Jul. 21, 1992 [DE] Fed. Rep. of Germany ....... 4223889

[51] Int. Cl.$^5$ ................ C07C 41/01; C07C 41/28; C07C 41/50
[52] U.S. Cl. .................... 568/596; 568/603
[58] Field of Search ................ 568/596, 603

[56] References Cited

U.S. PATENT DOCUMENTS 2,799,709 7/1957 Isler et al. .
2,879,278 3/1959 Clauson-Kaas ................ 260/347.8
4,098,827 7/1978 Rosenberger .

FOREIGN PATENT DOCUMENTS 747281 3/1956 Fed. Rep. of Germany .
67870 4/1951 Netherlands .

OTHER PUBLICATIONS

Scheeren et al., Recueil des Travaux Chimiques des Pays–Bas, vol. 94, No. 8, Aug. 1975, pp. 196–198.
*Methoden Der Organischen Chemie (Houben–Weyl)* Band VI/3, 1965, pp. 221–222.

*Primary Examiner*—Howard T. Mars
*Attorney, Agent, or Firm*—Keil & Weinkauf

[57] ABSTRACT

An improved process for preparing E,Z-butenedial bis(dialkyl acetals) by reacting the corresponding 2,5-dialkoxy-2,5-dihydrofurans with the corresponding lower alkanols in the presence of an acid at elevated temperature entails carrying out the reaction in the presence of approximately equimolar amounts of a trialkyl orthoformate and in the presence of catalytic amounts of a strong mineral acid or of a strong organic acid.

4 Claims, No Drawings

PREPARATION OF E,Z-BUTENEDIAL BIS(DIALKYL ACETALS)

The present invention relates to an improved process for preparing E,Z-butenedial bis(dialkyl acetals) of the formula I

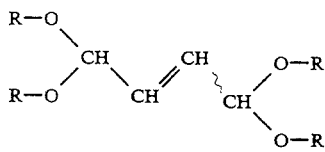

where R is —CH$_3$, —C$_2$H$_5$ or —C$_3$H$_7$, starting from the corresponding 2,5-dialkoxy-2,5-dihydrofurans.

Electron-rich alkenes like butenedial bis(dialkyl acetals), often also called tetraalkoxy-2-butenes, have interesting properties in addition and cycloaddition reactions with numerous electrophilic reactants.

Thus, for example, Z-butenedial bis(diethyl acetal) can be converted by the process of CH 321 106 by double enol ether condensation with 1-propenyl ethyl ether and subsequent hydrolysis in good yields into 2,7-dimethyl-2,4,6-octatrienedial. This C$_{10}$ dialdehyde is a favored intermediate for carotenoid syntheses (cf. DE 28 01 908).

The processes hitherto disclosed for the preparation of 1,1,4,4-tetraalkoxy-2-butenes are unsuitable for industrial preparation. Thus, for example, GB 747,281 discloses a process in which furan can be converted with bromine and an alkanol under anhydrous conditions at below $-25°$ C. into 1,1,4,4-tetraalkoxy-2-butenes. However, this process is too technically elaborate and costly in energy and is not environmentally friendly either.

Furthermore, Recueil, J. of the Royal Netherlands Chem. Sec. 94/8 (1975) 196-98 describes a process for preparing cis-1,1,4,4-tetramethoxy-2-butene in which 2,5-dimethoxy-2,5-dihydrofuran is refluxed with HCOOH in methanol for 8 hours. The disadvantage of this process is that the yields are, despite the long reaction times, only about 45% of theory.

It is an object of the present invention to develop a process for preparing 1,1,4,4-tetraalkoxy-2-butenes in which the prior art disadvantages are eliminated, i.e. the required compounds are obtained in good yields in a simpler and more environmentally friendly manner.

We have found that this object is achieved by a process for preparing E,Z-butenedial bis(dialkyl acetals) of the formula I

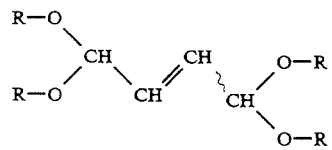

where R is —CH$_3$, —C$_2$H$_5$ or —C$_3$H$_7$, by reacting the 2,5-dialkoxy-2,5-dihydrofuran of the formula II

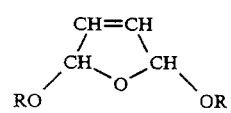

where R has the abovementioned meanings, with the corresponding alkanol of the formula III R OH (III) where R has the abovementioned meanings, in the presence of an acid at elevated temperature, wherein the reaction is carried out in the presence of approximately equimolar amounts, i.e. about 0.9–1.5 mol per mol of the furan of the formula II, of the corresponding trialkyl orthoformate of the formula IV $$HC(OR)_3 \quad (IV)$$

where R has the abovementioned meanings, and in the presence of catalytic amounts of a mineral acid or of a strong organic acid, neither of which attacks the reactants in another way, as catalyst.

The process according to the invention takes place particularly advantageously when it is carried out in the presence of an organic sulfonic acid, in particular in the presence of p-toluenesulfonic acid, as catalyst.

The 2,5-dialkoxy-2,5-dihydrofurans of the formula II required as starting compounds are readily available industrially as intermediates for preparing the biocide succinaldehyde and are obtainable industrially in a straightforward manner by, for example, oxidizing furan electrochemically in alkanols, The trialkyl orthoformate of the formula IV is advantageously trimethyl orthoformate, but it is also possible to use triethyl orthoformate or even tripropyl orthoformate.

The orthoformates serve to eliminate water and are therefore employed in approximately equimolar amounts, i.e. in amounts of about 0.9–1.5, preferably 1.0–1.2, mol per mol of the furan of the formula II.

The preferred alkanol of the formula III has the same alkyl radical as the furan of the formula II. Although it is also possible to employ any desired alkanols, in this case the product is not defined but comprises butenedial bis(dialkyl acetals) with different alkyl substituents in one molecule.

The process according to the invention is particularly advantageous when 2,5-dimethoxy-2,5-dihydrofuran of the formula II is reacted with methanol in the presence of trimethyl orthoformate to prepare E,Z-butenedial bis(dimethyl acetal) of the formula I.

The alkanol of the formula III is generally used in amounts of 2–10, preferably 3–6, mol of alkanol per mole of furan of the formula II.

Suitable catalysts for the process according to the invention are mineral acids or organic acids which have a pKa of about $-9$ to $+3.77$ and which do not under the reaction conditions attack the reactants in other ways. For definition of the pKa, reference is made to Ullmanns Encyklopädie der technischen Chemie, Volume 15, page 2. Suitable examples are mineral acids such as concentrated sulfuric acid (pKa=$-3$), expediently 90–98% by weight sulfuric acid, orthophosphoric acid (pKa=2.09), expediently 85–90% by weight phosphoric acid, concentrated hydrochloric acid (pKa=$-6$), perchloric acid (pKa=$-9$) and strong organic acids such as trichloroacetic acid (pKa=0.92), formic acid (pKa=3.77), oxalic acid (pKa=1.46) and organic sulfonic acids. Suitable sulfonic acids are: aliphatic sulfonic acids, especially the lower alkanesulfonic acids such as methanesulfonic acid, ethanesulfonic acid, 1-propanesulfonic acid, 2-propanesulfonic acid and trifluoromethanesulfonic acid; the alicyclic sulfonic acids such as camphorsulfonic acid, and the aromatic sulfonic acids such as toluenesulfonic acids, especially p-toluenesulfonic acid, the naphthalenesulfonic acids, especially 1-naphthalenesulfonic acid and 2-naphthalenesulfonic acid, benzenesulfonic acid, and acid ion exchangers containing sulfo groups. The acids which are particularly preferred in the process according to the invention are the relatively low-cost, strong inorganic acids such as sulfuric acid and phosphoric acid, and the strong organic acids of relatively low corrosivity, such as p-toluenesulfonic acid.

The acid catalyst is generally used in amounts of about $10^{-5}$ to $5 \times 10^{-2}$, preferably from $10^{-4}$ to $10^{-2}$, mol per mol of 2,5-dimethoxy-2,5-dihydrofuran in the case of the inorganic acid, and from $10^{-5}$ to $10^{-1}$, preferably from $10^{-4}$ to $10^{-2}$, mol in the case of the organic acid.

The procedure for the reaction is generally such that a solution of reactants I to IV is mixed with the acid catalyst, and the mixture is refluxed.

The reaction generally takes from 1 to 10, preferably 2 to 6, hours. The progress of the reaction can be followed by gas chromatography.

The process according to the invention can be used to prepare in a straightforward manner and in good yields the E,Z-butenedial bis(dialkyl acetals) of the formula I which are in demand as intermediates for carotenoid syntheses.

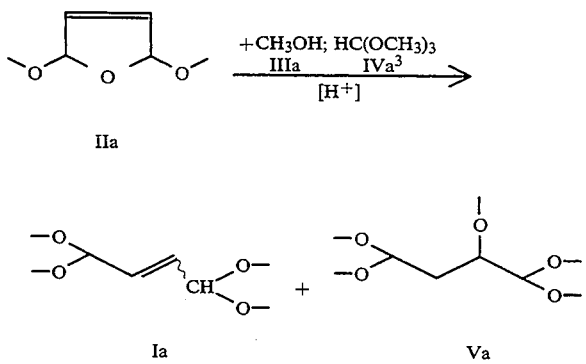

0.2 g of p-toluenesulfonic acid was added to a solution of 265.3 g (2 mol) of 2,5-dimethoxy-2,5-dihydrofuran (IIa), 384 g (12 mol) of methanol (IIIa) and 214.4 g (2 mol) of trimethyl orthoformate (IVa) in a 2 l glass reactor, and the mixture was then heated to 65° C. over the course of 20 minutes (min) and finally refluxed for 2 hours (h). The reaction was followed by gas chromatography (percentage areas). The following table shows the course of the reaction to form E,Z-butenedial bis(dimethyl acetal) (Ia) and 1,1,2,4,4-pentamethoxybutane (Va).

| Reaction time [min] | HC(OCH$_3$)$_3$ [% area] | IIa [% area] | Ia [% area] | Va [% area] |
|---|---|---|---|---|
| 0 | 29.5 | 59 | 9.4 | |
| 30 | 18.2 | 33 | 47 | 0.6 |
| 60 | 14.0 | 26 | 57 | 1.0 |
| 90 | 11.0 | 21 | 65 | 1.8 |
| 120 | 7.7 | 15 | 72 | 2.9 |

The reaction was then stopped by adding 1.9 g of a 30% strength solution of CH$_3$ONa in methanol, excess methanol was removed by distillation under atmospheric pressure, and the residue was fractionated through a 30 cm packed column under greatly reduced pressure. The resulting fractions had the following compositions according to gas chromatography (GC):

TABLE 1

| No. | Fraction Boiling range [°C., mbar] | Amount [g] | HC(CH$_3$O)$_3$ [% area] | IIa [% area] | Ia [% area] | Va [% area] | Ia [g] |
|---|---|---|---|---|---|---|---|
| 1 | 63/100, 29 | 10.6 | 8.7 | 85.2 | 4.5 | | |
| 2 | 67–85/130, 29 | 19.1 | 0.3 | 94.2 | 4.5 | | |
| 3 | 86/130, 29 | 16.8 | 0.3 | 45.1 | 53.4 | 0.1 | |
| 4 | 99–105/138, 29 | 233.2 | | 1.14 | 96.3 | 0.9 | 234.6 |
| 5 | 107/145, 29 | 27.3 | | | 83.7 | 13.9 | 23 |
| 6 | residue | 8.2 | | | 22.0 | 76.0 | |
| | | | | | | Total | 257.6 g |

Fractions 4 and 5 together comprise 257.6 g of the required E,Z-butenedial bis(dimethylacetal), corresponding to 73% of theory. Fractions 1 to 3 contain 34.6 g of the precursor 2,5-dimethyoxy-2,5-dihydrofuran (IIa) which can be returned to the process. The selectivity of the reaction is thus 85%.

EXAMPLE 2

0.1 g of concentrated H$_2$SO$_4$ was added to a solution of 198 g (1.5 mol) of 2,5-dimethoxy-2,5-dihydrofuran in a mixture of 288 g (9 mol) of methanol and 191 g (1.8 mol) of trimethyl orthoformate. The mixture was then refluxed (69° C.) for 4 h. The reaction was stopped by adding 1.5 g of a 30% strength solution of CH$_3$ONa in methanol. Methanol and methyl formate were then removed by distillation under atmospheric pressure. The residue was fractionally distilled under about 30 mbar (96°–103° C.). 198 g of 98% pure butenedial bis(dimethyl acetal) were obtained, corresponding to a yield of 74% of theory. Unreacted 2,5-dimethoxy-2,5-dihydrofuran was isolated as fore-run and can be employed in a new reaction.

EXAMPLES 3 to 9

In each of these the amounts of 2,5-dimethoxy-2,5-dihydrofuran (IIa), methanol, trimethyl orthoformate and acid catalyst which are shown in Table 2 were heated together in a 2 1 glass reactor initially at 65° C. for 20 min and then under reflux for the times indicated in the table. The yields of E,Z-butenedial bis(dimethyl acetal) are indicated in the last column of Table 2. Since the reaction takes place with a conversion of about 90%, the resulting selectivities are about 80–85%.

TABLE 2

| Ex. | IIa [mol] | HC(CH$_3$O)$_3$ [mol] | CH$_3$OH [mol] | Acid catalyst [g] | Reaction time [h] | Yield [%] |
|---|---|---|---|---|---|---|
| 3 | 2 | 2 | 6 | 0.1 g conc. H$_2$SO$_4$ | 4 | 74–78 |
| 4 | 2 | 2 | 9 | 4 g conc. | 5 | 72 |

TABLE 2-continued

| Ex. | IIa [mol] | HC(CH3O)3 [mol] | CH3OH [mol] | Acid catalyst [g] | Reaction time [h] | Yield [%] |
|---|---|---|---|---|---|---|
| 5 | 2 | 2 | 6 | HCl 1 g conc. | 6 | 72 |
| 6 | 2 | 2 | 6–12 | 0.2 g H3PO4 | 2 | 75 |
| 7 | 2 | 2 | 6 | 0.2 g p-TosOH | 2 | 74 |
| 8 | 2 | 2 | 6 | 0.2 g CF3—SO3H | 2 | 73 |
| 9 | 2 | 2 | 6–12 | 1 g CH3—SO3H Sicapent (P2O5 on SiO2) | 6 | 70 |

COMPARATIVE EXAMPLE 0.2 g of p-toluenesulfonic acid was added to a solution of 265.3 g (2 mol) of 2,5-dimethoxy-2,5-dihydrofuran in 192 g (6 mol) of methanol, and the mixture was then refluxed for 1 h. Subsequently, methanol was removed by distillation through a 10 cm Vigreux column over the course of 1.5 h and, during this, a further 6 mol of methanol were slowly added (removal of water). After a total reaction time of 8 h, the methanol was completely removed, and the residue was fractionated through the Vigreux column. 60% of the 2,5-dimethoxy-2,5-dihydrofuran was recovered unreacted. The yield of the required butenedial bis(dimethyl acetal) was only about 35% of theory.

We claim:

1. A process for preparing E,Z-butenedial bis(dialkyl acetals) of the formula I

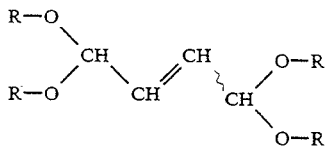 (I)

where R is —CH3, —C2H5 or —C3H7, by reacting the 2,5-dialkoxy-2,5-dihydrofuran of the formula II

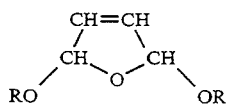 (II)

where R has the abovementioned meanings, with the corresponding alkanol of the formula III R OH (III) where R has the abovementioned meanings, in the presence of a catalyst selected from the group consisting of a mineral acid and a strong organic acid at elevated temperature, wherein the reaction is carried out in the presence of 0.9–1.5 mol of the corresponding trialkyl orthoformate of the formula IV

HC(OR)3 (IV)

where R has the abovementioned meanings, per mol of the furan of the formula II, and in the presence of catalytic amounts of said mineral acid or of said strong organic acid, neither of which attacks the reactants.

2. A process as claimed in claim 1, wherein 2,5-dimethoxy-2,5-dihydrofuran of the formula II is reacted with methanol in the presence of trimethyl orthoformate to prepare E,Z-butenedial bis(dimethyl acetal) of the formula I.

3. A process as claimed in claim 1, wherein the reaction is carried out in the presence of an organic sulfonic acid as catalyst.

4. A process as claimed in claim 3, wherein the reaction is carried out in the presence of p-toluenesulfonic acid as catalyst.

* * * * *